United States Patent

Woolnough et al.

[11] Patent Number: 5,941,913
[45] Date of Patent: Aug. 24, 1999

[54] ABOVE-KNEE LOWER LIMB PROSTHESIS AND A SHIN COMPONENT FOR THE PROSTHESIS

[75] Inventors: Victor James Woolnough, Hampshire; Andrew John Sear Evans, Surrey, both of United Kingdom

[73] Assignee: Chas. A Blatchford & Sons Limited, United Kingdom

[21] Appl. No.: 08/948,004

[22] Filed: Oct. 9, 1997

[30] Foreign Application Priority Data

Oct. 10, 1996 [GB] United Kingdom .................. 9621137

[51] Int. Cl.$^6$ .............................. A61F 2/64; A61F 2/74; A61F 2/66
[52] U.S. Cl. .................................. 623/47; 623/27; 623/53
[58] Field of Search .................... 623/44, 27, 52, 623/38, 47, 32, 50, 39

[56] References Cited

U.S. PATENT DOCUMENTS

| | | | |
|---|---|---|---|
| 4,360,931 | 11/1982 | Hampton | 3/7 |
| 4,397,048 | 8/1983 | Brown et al. | 623/35 |
| 4,547,913 | 10/1985 | Phillips | 623/27 |
| 4,959,073 | 9/1990 | Merlette | 623/55 |
| 4,994,086 | 2/1991 | Edwards | 623/26 |
| 5,181,932 | 1/1993 | Phillips | 623/52 |
| 5,181,933 | 1/1993 | Phillips | 623/55 |
| 5,217,500 | 6/1993 | Phillips | 623/38 |
| 5,290,319 | 3/1994 | Phillips | 623/56 |
| 5,486,209 | 1/1996 | Phillips | 623/52 |
| 5,509,938 | 4/1996 | Phillips | 623/56 |
| 5,514,185 | 5/1996 | Phillips | 623/52 |
| 5,514,186 | 5/1996 | Phillips | 623/52 |
| 5,593,445 | 1/1997 | Waits | 623/18 |
| 5,593,457 | 1/1997 | Phillips | 623/52 |
| 5,704,946 | 1/1998 | Greene | 623/44 |
| 5,746,773 | 5/1998 | Litting | 623/35 |

FOREIGN PATENT DOCUMENTS

| | | |
|---|---|---|
| 1233003 | 2/1988 | Canada . |
| 2 202 448 | 9/1988 | United Kingdom . |
| 2 265 089 | 9/1993 | United Kingdom . |
| WO 94/22398 | 10/1994 | WIPO . |
| WO 94/25488 | 9/1995 | WIPO . |

Primary Examiner—Mickey Yu
Assistant Examiner—Alvin Stewart
Attorney, Agent, or Firm—Fish & Richardson P.C.

[57] ABSTRACT

A single-piece fibre-reinforced plastics shin component for a lower limb prosthesis for an above-knee amputee has an energy storing blade and, integrally formed therewith, a shin cradle in the form of a channel section which has a pair of pivot supports formed as flanges extending away from one of the major surfaces of the blade. Each flange has a pair of holes defining transverse pivot axes, one of which is a knee axis and the other of which is a pivot axis for mounting the distal end of a knee movement control unit. These holes together define a longitudinal axis which is generally parallel to and to the anterior of the blade. The blade merges smoothly into the channel section and, over a distal end portion, is straight and of constant cross-section to allow the blade to be cut to length to suit the amputee.

25 Claims, 2 Drawing Sheets

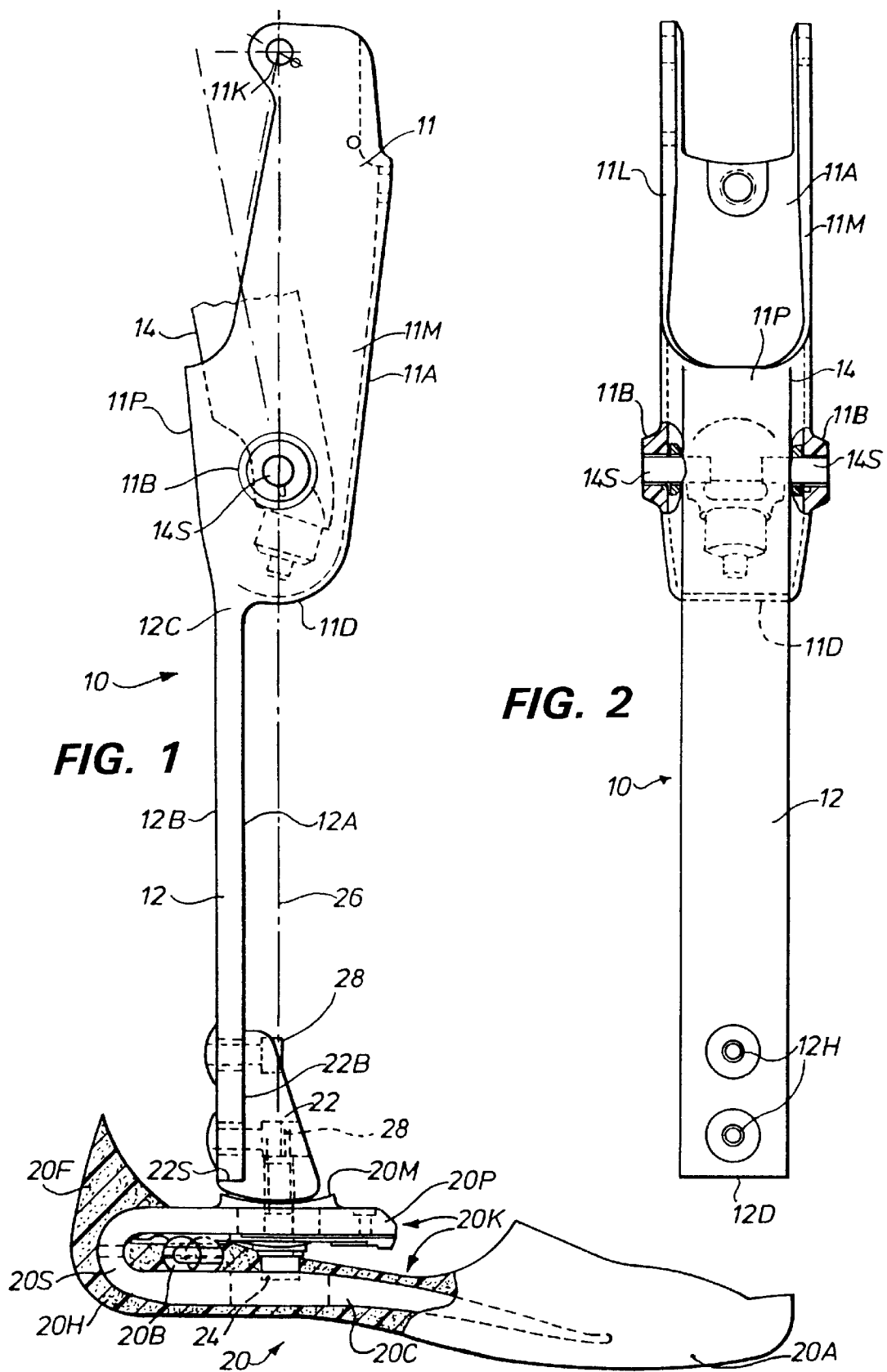

ABOVE-KNEE LOWER LIMB PROSTHESIS AND A SHIN COMPONENT FOR THE PROSTHESIS

BACKGROUND OF THE INVENTION

This invention relates to an above-knee lower limb prosthesis, and to an energy-storing shin component for the prosthesis.

An energy-storing lower limb prosthesis is known from U.S. Pat. No 4,547,913 (Phillips). This device provides an integral shin member and forefoot in the form of a single blade of fibre-reinforced material, the shin member extending generally axially of the prosthesis with the forefoot cantilevered in the anterior direction and with a curved connection between shin member and forefoot in an ankle region of the prosthesis. The major surfaces of the blade forming the shin member extend in the medial-lateral direction. A second blade, also with its major surfaces extending in a medial-lateral direction, is rigidly connected to the shin member in the ankle region and extends in the posterior direction to form a resilient heel member. Since the shin member is substantially planar and extends substantially vertically with a cross-section having a high area moment of inertia about an axis generally aligned in the anterior-posterior direction and a relatively low area moment of inertia about a horizontal axis generally aligned in the medial-lateral direction, it acts as a leaf spring storing and releasing energy during the stance phase, by anterior-posterior bending whilst being comparatively rigid with respect to transverse bending moments. This prosthesis is particularly useful for active amputees, including those wishing to take part in sports activities.

A disadvantage of this known device is that the energy-storing capabilities are achieved at the expense of versatility, in the sense that a wide range of sizes and stiffnesses must be produced to suit different amputees, particularly with regard to foot size. Although in the case of above-knee lower limb prostheses, the device may be connected to different knee mechanisms, for instance by means of clamps or flanges attached to the proximal end of the shin member, in some situations, the length of the shin member becomes comparatively short with consequent loss of energy-storing capacity. This is particularly the case with knee mechanisms incorporating an hydraulic or pneumatic swing phase control unit.

It is an object of this invention to provide a versatile shin component.

SUMMARY OF THE INVENTION

According to a first aspect of this invention we provide a single piece fibre-reinforced shin component for an above-knee lower limb prosthesis comprising an elongate resilient energy-storing blade and, in the region of one end of the blade and integrally formed with the blade, at least one pivot support extending away from at least one of the major surfaces of the blade to define a plurality of pivot axes for pivotally connecting the component to an upper prosthesis component, the pivot axes extending transversely and generally parallel to the said major surfaces and spaced apart from each other in the longitudinal direction of the blade. The or each pivot support may comprise a flange extending in an anterior-posterior direction from a respective longitudinal edge of the blade and away from a major face of the blade. Preferably, the component has two such flanges, each having a pair of pivot features defining a pair of medial-lateral pivot axes extending from one flange to the other, one axis defining a knee axis of rotation, the other a connection axis for a piston and cylinder knee flexion control unit. The preferred shin component has a pair of such pivot supports in the form of a shin cradle integrally formed at one end of the blade for pivotal connection to an upper limb component.

The flanges may forms together with an anterior wall which is an extension of the blade, a cradle of generally U-shaped cross-section, the flanges extending away from a notional surface which is a projection of one or other of the major faces of the blade. In particular, in one embodiment of the invention, the shin component has an energy-storing blade merging into an anterior wall of a generally U-shaped channel section formed by the said wall and two posteriorly extending side walls or flanges which extend generally parallel to each other away from the notional surface, both on the same side of the latter.

The pivot supports of the or each flange define a longitudinal axis and in one embodiment in which the cradle or channel section has an anterior wall, the blade and the anterior wall merge smoothly one into the other, with the proximal portion of the blade curving to cross the longitudinal axis. In other words, the main part of the blade is on one side (the posterior) of the longitudinal axis, while the cradle anterior wall is on the other (anterior) side.

According to another aspect of the invention, we provide an above-knee lower limb prosthesis including a combination of the above shin component and a demountable artificial foot having a foot keel extending in the posterior-anterior direction and an upwardly projecting mounting member for receiving a distal end portion of the shin component blade.

In the preferred embodiment of the invention, this construction allows use of a blade of sufficient length to provide good energy-storing performance in conjunction with swing phase control whilst allowing for shin length adjustment by cutting the distal end portion of the shin component to a required length and mounting on the distal end portion an artificial foot of required size and characteristics. Integral construction of the blade and the shin cradle yields high strength at the proximal end of the blade whilst providing maximum blade length within the space available.

Assembly of the prosthesis includes the steps of cutting the distal end portion of the blade to a required length, selecting an artificial foot of the required size and configuration, and attaching the foot to the blade end portion by means of a mounting member forming part of the foot, the attachment being formed by, e.g., one or more bolts passing through the mounting member and the blade.

Typically, the cradle is dimensioned and configured to receive a piston and cylinder assembly for knee joint control, the cylinder being housed between medial and lateral walls of the cradle and pivotally mounted in bosses formed in those walls.

The invention will now be described below by way of example with reference to the drawings.

BRIEF DESCRIPTION OF THE DRAWINGS

In the drawings:

FIG. 1 is a diagrammatic side-elevation of a lower limb prosthesis in accordance with the invention;

FIG. 2 is a posterior elevation of the shin component of the prosthesis shown in FIG. 1;

DETAILED DESCRIPTION OF THE PREFERRED EMBODIMENTS

Figure 3:
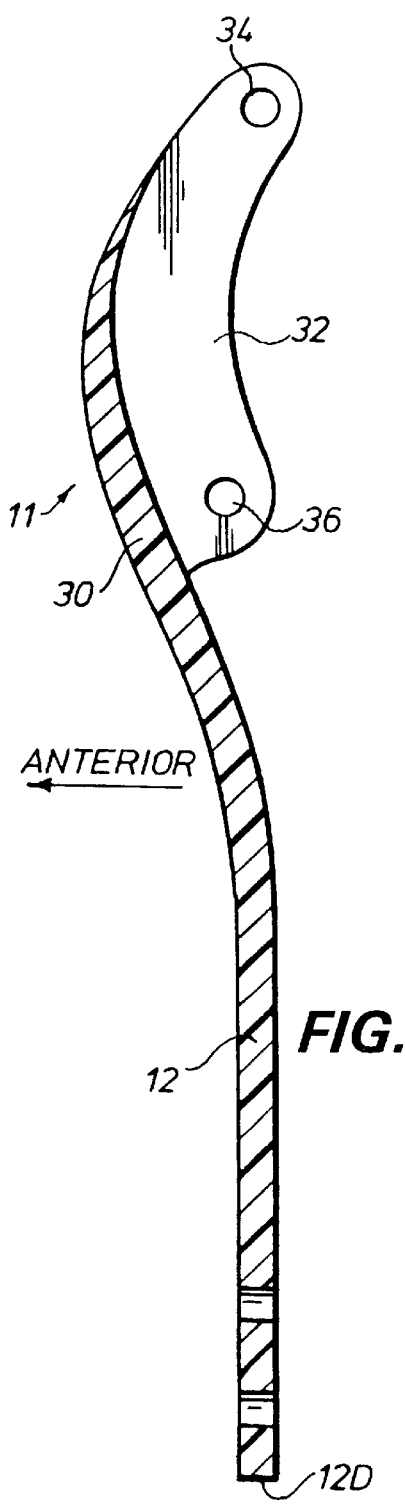
FIG. 3 is a longitudinal cross-section (in an anterior-posterior plane) of an alternative shin component in accordance with the invention.

Referring to FIGS. 1 and 2, a high activity energy-storing lower limb prosthesis for an above-knee amputee has a shin component 10, and a foot component 20 secured to the shin component.

The shin component 10 is a single-piece moulded carbon-fibre-reinforced plastics component having a shin cradle 11 and an integrally formed energy-storing blade 12 with a proximal end connected to a distal portion of the cradle 11, generally in a posterior region of the cradle 11 so as to form a distal continuation of a posterior wall 11P, of the cradle 11. In the lower, distal region of the cradle 11, the posterior wall 11P, in conjunction with anterior, medial, and lateral cradle walls 11A, 11M, and 11L form a cavity which is closed off at the distal end by a cradle distal end portion 11D and which houses the lower end of a piston and cylinder assembly for controlling flexion and/or extension of the prosthesis at the knee. The piston and cylinder assembly is shown by reference 14 in FIG. 1, and is pivotally attached by stub shafts 14S which are rotatably housed in bosses 11B in the medial and lateral walls respectively of the cradle 11.

In a proximal region of the shin cradle 11, the medial and lateral walls 11M and 11L have bores 11K for pivotal mounting of the cradle 11 on a knee chassis forming part of an upper limb component (not shown). In general, the axis of bores 11K defines the knee axis of rotation.

In this embodiment, the shin component blade 12 is of rectangular cross-section, having its major surfaces 12A, 12B extending in a medial-lateral direction to allow resilient deformation in response to bending moments acting in the anterior-posterior plane whilst being substantially rigid with respect to bending moments in the medial-lateral plane.

In this preferred embodiment of the invention, the cross-section of the blade is constant over the major part of she blade length, and is, preferably, constant over its whole length between the distal end 12D of the blade 12 and its connection 12C with the shin cradle. The width of the blade is between 30 and 50 mm, whilst its thickness is between 7.5 and 15 mm. In this preferred embodiment, the width and thickness are approximately 40 mm and 10 mm respectively. Typically, the overall length of the blade is between 200 and 300 mm.

The blade has a plain distal end portion in the sense that the constant cross-section is maintained to the extreme distal end 12D to allow the blade to be cut to length to suit individual amputees so that the prosthetist is not required to select a shin component from a large range of shin components of different lengths.

The prosthesis includes an energy-storing artificial foot of the configuration disclosed in British Patent Specifications Nos. 216423 and 2252251, the disclosure of which is incorporated herein by reference.

Foot 20 has a fibre-reinforced plastics keel 20K with an upper mounting plate 20P extending in the anterior-posterior direction, a lower cantilever portion 20C extending from a heel region 20H into an anterior portion 20A of the foot, and a posterior keel portion 20S of C-shaped configuration connecting the upper mounting plate 20P to the cantilever portion 20C in the heel region 20H. Keel 20K acts as an energy-storing spring the stiffness of which can be adjusted, as described in the above-mentioned prior patent specifications, by adjusting the anterior-posterior position of a transverse fulcrum bar 20B located between the distal surface of the upper mounting plate and the proximal surface of the cantilever portion, as shown in FIG. 1.

The mounting plate 20P carries an adjustable shin blade mounting member 22 on a proximally directed concave serrated surface 20M, the mounting member 22 having a convex serrated bearing surface 22B of corresponding radius about a medial-lateral axis. This adjustment interface between the mounting plate 20P of the foot and the mounting member 22 allows adjustment of the angle of the foot about the said axis, providing the possibility of heel height variation. Once a required heel height has been set, the mounting member is rigidly secured to the keel by a bolt 24 centred on the longitudinal axis 26 of the prosthesis.

When the shin component blade 12 has been cut to a required length, fixing holes 12H are drilled so that when the distal end portion of the blade 12 is located in a corresponding recess of the mounting member 22, bolts 28 can be passed through holes in the mounting member, and through the holes 12H drilled in the blade so as to secure the blade to the mounting member 22. The recess has a distal-proximal planar surface 22B for receiving the anterior surface 12A of the distal end portion of the blade, and is terminated by a shoulder 22S which abuts the distal end 12B (see FIG. 2) of blade 12 when it is located in the recess, thereby defining the overall length of the prosthesis.

The keel 20K of the foot 20 is at least partly surrounded by a moulded foam cosmesis 20F, although alternative ground-contacting members may be provided on the keel, depending on requirements.

Provision of a demountable interface between the blade 12 and foot 20 permits alternative foot configurations to the combined with the shin component, the integral construction of the blade 12 and cradle 11 allowing such foot interchangeability whilst retaining a blade of considerable length and hence superior energy-storing capacity in a prosthesis employing a piston and cylinder knee movement control unit such as unit 14.

Bolt 24 which secures the mounting member 22 to the foot keel 20K, as well as the knee axis defined by the bones 11K both lie on the longitudinal axis 26 of the prosthesis as do, in this embodiment, the pivot shafts 14S connecting the piston and cylinder assembly 14 to the lower part of the shin cradle 11. It will be noted that the shin component blade 12 is to the posterior of and parallel to axis 26. This has the effect of increasing the strain energy which can be stored in the blade 12 due to the increased moment produced by a ground reaction force in the forefoot (as occurs when the forefoot is loaded during at least the latter part of the stance phase). The strain energy, U, for a beam in pure bending is given by $U=M^2L/2EI$ where E is the flexural modulus of the blade material, and I is the second moment of area of the blade section. The moment M is given by FX, where F is the applied load and X is the anterior distance of the point at which load F is applied from the longitudinal axis of the blade. It follows that, for a given load F, the stored strain energy is proportional to $X^2$. This square law illustrates the benefit of locating the blade to the posterior of the limb axis 26.

In an alternative shin components shown in FIG. 3, the cradle 11 has an anterior wall 30 formed by the distal end of the blade 12. The cradle has posteriorly extending medial and lateral side walls joined to the longitudinal sides of the anterior wall 30. Only one of these side walls 32 is visible n FIG. 3. In a transverse horizontal cross-section, the cradle 11 is U-shaped and the anterior wall 30 may be curved so as to merge into the side walls without perceptible corners.

Each side wall 32 is in the form of an ear having a pair of holes 34, 36 spaced apart from each other longitudinally, these holes serving to define the knee axis of rotation and the pivot axis for the distal end of a swing phase control unit.

As in the embodiment of FIGS. 1 and 2, the blade 12 is positioned so as to be generally to the posterior of the limb axis, here defined by a line joining the axes of the holes 34, 36. In this case, however, the proximal portion of the blade is curved to cross the limb axis and then to form the anterior wall 30 of the cradle 11.

Figure 4:
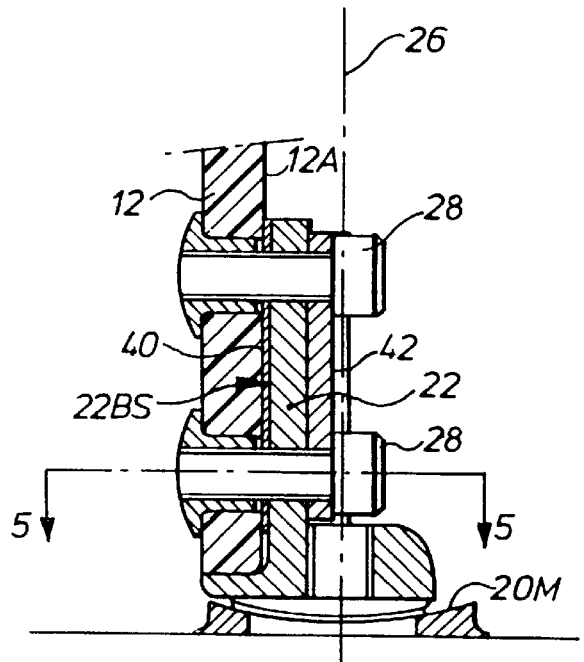
FIG. 4 is a longitudinal cross-section of an alternative shin-foot connection allowing rotational adjustment about both medial-lateral and longitudinal axes.
Figure 5:
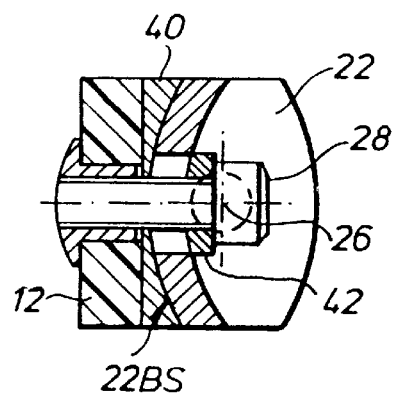
FIG. 5 is a transverse cross-section on the line 4—4 in FIG. 4.

Referring to FIGS. 4 and 5, an alternative structure for connecting the foot 20 to the shin component blade 12 allows adjustment of the angle of the foot not only about a medial-lateral axis, but also about a longitudinal axis coincident with or parallel to the longitudinal axis 26 of the prosthesis, thereby effecting a toe-in/toe-out. In this case the upper portion of the mounting member 22 has a cylindrical convex posterior bearing surface 22BS centred on an axis parallel and anterior with respect to the prosthesis axis 26. A spacer 40 with a correspondingly cylindrical concave anterior surface and a planar posterior surface is clamped between the mounting member 22 and the anterior surface 12A of the blade 12 when the bolts 28 are tightened. An elongated washer 42 with a convex cylindrical posterior surface transfers the clamping load from the heads of the bolts 28 to a concave cylindrical anterior surface of the upper portion of the mounting member 22. It will be appreciated that by slackening the bolts 28, the upper portion of the mounting member 22 having the cylindrical convex and concave surfaces, may be moved from side to side, thereby effecting a rotation of the foot about a vertical axis to the anterior of the limb axis 26. Once a required degree of toe-in or toe-out has been achieved, the bolts 28 are once again tightened.

What is claimed is:

1. A single-piece fibre-reinforced plastics shin component for an above-knee lower limb prosthesis comprising an elongate resilient energy-storing blade having major surfaces and, in the region of one end of the blade and integrally formed with the blade, at least one pivot support extending away from one of the major surfaces to define a plurality of pivot axes for pivotally connecting the component to an upper prosthesis component, the pivot axes extending transversely and generally parallel to the major surfaces and spaced apart from each other in the longitudinal direction of the blade.

2. A shin component according to claim 1, wherein the pivot support comprises a flange joined to a longitudinal edge of the blade and extending in a longitudinal plane oriented generally perpendicularly to the blade.

3. A shin component according to claim 1, having at least one pair of the said pivot supports joined to opposite respective longitudinal edges of the blade and extending away from the same said major surface of the blade to define a cradle for a swing phase control unit.

4. A shin component according to claim 3, having two pivot supports in registry with each other and joined to opposite longitudinal edges of the blade, each pivot support having a pair of holes each of which defines a respective one of two pivot axes extending between the pivot supports.

5. A shin component according to claim 4, wherein one of the pivot axes is a knee axis of rotation and the other defines a pivotal connection axis for a swing phase control unit.

6. A shin component according to claim 1, having a pair of spaced apart flanges extending on one side of one of the major surfaces of the blade, and a wall between the flanges which forms a continuation of the blade, and wherein each of the flanges has a pair of holes defining respective pivot axes extending parallel to each other between the flanges, and wherein the blade lies on one side of a longitudinal line joining the holes of the said pair of holes.

7. A shin component according to claim 6, further comprising a connecting wall interconnecting the flanges to form a cradle of substantially U-shaped cross-section, the blade merging smoothly into the connecting wall.

8. A shin component according to claim 7, wherein the connecting wall lies on the opposite side of the said longitudinal line, with the blade being curved so as to cross over the line from one side to the other in merging with the connecting wall.

9. A shin component according to claim 1, having a pair of pivot supports in the form of a shin cradle integrally formed with the blade.

10. A shin component according to claim 9, wherein the blade has a distal end portion remote from the cradle which end portion is of constant cross-section to allow length adjustment by cutting without altering the attachment cross-section for attaching a foot prosthesis.

11. A shin component according to claim 10, wherein the blade is of constant cross-section over the major part of its length including the distal end portion, and wherein the blade has a straight longitudinal axis.

12. A shin component according to claim 9, wherein the shin cradle has a medial wall, a lateral wall and a connecting wall between the medial and lateral walls, and wherein the blade forms a distally extending continuation of the connecting wall, with the major surfaces of the blade extending in a medial-lateral direction.

13. A shin component according to claim 12, wherein the connecting wall is a posterior wall, and wherein distal portions of the medial and lateral walls lie generally to the anterior of the blade.

14. A shin component according to claim 9, wherein the shin cradle has anterior, posterior, medial and lateral walls which are joined together to form an interior space which is closed at the distal end of the cradle by a distal end wall connected to and extending generally anteriorly from the blade.

15. A shin component according to claim 1, wherein the shin cradle has an upper connection feature defining a knee pivot axis.

16. A shin component according to claim 15, wherein the shin cradle further includes a lower connection feature for pivotally mounting a piston and cylinder knee control unit horsed within the cradle.

17. A shin component according to claim 1, wherein the blade is of constant medial-lateral width and, at least in a distal end portion thereof, of constant cross-section.

18. A shin component according to claim 1, wherein the major surfaces of the blade are planar and parallel to each other.

19. An above-knee lower limb prosthesis including the combination of a shin component according to claim 1 and a demountable artificial foot having a foot keel extending in a posterior-anterior direction and an upwardly projecting mounting member for receiving a distal end portion of the shin component blade.

20. A prosthesis according to claim 19, wherein the mounting member is adjustably connected to the keel to allow heel-height adjustment, and is connected to the keel predominantly to the anterior of the blade.

21. A prosthesis according to claim 19, wherein the mounting member is clamped to the blade distal end portion by at least one bolt passing through the mounting member and the blade in an anterior-posterior direction.

22. A prosthesis according to claim 19, wherein the keel is in the form of a leaf spring.

23. A prosthesis according to claim 22, wherein the keel has an upper mounting portion bearing the mounting member, a lower cantilever portion extending from a heel region of the foot to an anterior portion of the foot, and a posterior portion connecting the upper mounting portion to the cantilever portion in the heel region.

24. A prosthesis according to claim 19, wherein the mounting member has a planar bearing surface for receiving the blade and, adjacent a distal end of the bearing surface, an abutment surface for abutting an end surface of the blade.

25. A method of making an above-knee lower limb prosthesis comprising:

providing a shin component as defined in claim 1;

selecting a foot prosthesis of a required size and configuration, the foot prosthesis having a foot keel extending in an anterior-posterior direction and an upwardly extending mounting member shaped to receive a distal end portion of the shin component blade;

cutting the distal end portion of the blade to a required length; and mounting the foot to the shin component by securing the foot mounting member to the blade distal end portion.

* * * * *